(12) United States Patent
Leitner et al.

(10) Patent No.: US 6,720,281 B2
(45) Date of Patent: Apr. 13, 2004

(54) CHIRAL PHOSPHORUS LIGANDS AND THE USE THEREOF IN THE PRODUCTION OF OPTICALLY ACTIVE PRODUCTS

(75) Inventors: Walter Leitner, Mülheiim an der Ruhr (DE); Giancarlo Francio, Messina (IT); Felice Faraone, Messina (IT); Carmela G. Arena, Messina (IT)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 10/062,027

(22) Filed: Feb. 1, 2002

(65) Prior Publication Data
US 2003/0065181 A1 Apr. 3, 2003

Related U.S. Application Data

(63) Continuation-in-part of application No. PCT/EP00/07053, filed on Jul. 22, 2000.

(30) Foreign Application Priority Data

Aug. 3, 1999 (DE) .......................... 199 36 473

(51) Int. Cl.[7] .............. B01J 31/24; C07F 9/00
(52) U.S. Cl. ...................... 502/162; 546/23
(58) Field of Search .............. 546/21, 22, 23; 556/13, 19; 502/162; 568/300, 700; 562/1, 8

(56) References Cited

U.S. PATENT DOCUMENTS 5,556,849 A * 9/1996 Abrams et al. ............ 514/185

OTHER PUBLICATIONS

CA:133:1041619 abs of Angewandte Chemie International Edition by Francio et al 39(8) pp 1428–1430, 2000.*

* cited by examiner

*Primary Examiner*—Jean F. Vollano
(74) *Attorney, Agent, or Firm*—Norris McLaughlin & Marcus

(57) ABSTRACT

The present invention relates to novel chiral phosphorus compounds which can be readily prepared from quinoline derivatives as inexpensive starting compounds and have the general formula I

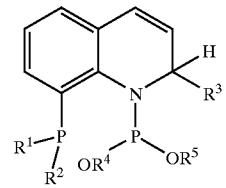

wherein $R^1$, $R^2$, $R^3$, $R^4$, $R^5$ are chiral or achiral organic residues which are derived from substituted or unsubstituted straight or branched chain or cyclic aliphatic or aromatic groups and which, in the case of the pairs $R^1/R^2$ and $R^4/R^5$, may be interconnected. Further, the invention relates to the use of chiral phosphorus compounds of general formula I as catalysts or catalyst components in processes for the preparation of optically active products.

10 Claims, No Drawings

CHIRAL PHOSPHORUS LIGANDS AND THE USE THEREOF IN THE PRODUCTION OF OPTICALLY ACTIVE PRODUCTS

This application is a continuation-in-part of PCT/EP00/07053, which was filed on Jul. 22, 2000, and not published in English under PCT Article 21(2). Pursuant to 35 USC §120, priority of the PCT is claimed. Pursuant to 35 USC §119, priority of German Patent Application No. DE 199 36473.7, filed on Aug. 3, 1999, is also claimed.

The present invention relates to novel chiral phosphorus compounds which can be readily prepared from quinoline derivatives, and their use as catalysts or catalyst components in processes for the preparation of optically active products.

Chiral phosphorus compounds are of great interest as catalysts or catalyst components ("ligands") for the enantioselective chemical synthesis of optically active products (Handbook of Enantioselective Catalysis with Transition Metal Compounds, Vol. II, VCH, Weinheim, 1993). Optically active products are of great economic importance as flavoring agents, cosmetics, plant protectants, food additives, pharmaceuticals, or in the preparation of high-tech materials, such as special plastics (Comprehensive Asymmetric Catalysis, Springer, Berlin, 1999). To date, despite of the wide variety of known chiral phosphorus compounds, only a few members have been put to use in industrial processes for the preparation of optically active products, because many ligands have serious disadvantages for technical applications. Many ligands, although exhibiting high enantioselectivities, form the desired chiral products with too low activities or insufficient chemo- or regioselectivities. Further, chiral phosphorus compounds which act as efficient ligands are often available only by tedious syntheses using expensive starting materials. In most efficient ligands, the chiral information which results in the selective formation of the optically active products is based on the use of chiral building blocks which are either derived from naturally occurring compounds or otherwise commercially available in an optically pure form. A structural variation in the chiral center for optimizing the phosphorus compound cannot be realized in a simple way in this case, and often only one of the two possible configurations is available. Therefore, there is a great need for novel chiral phosphorus compounds which can be synthesized in a simple and flexible way from readily available and inexpensive starting compounds and can be effectively employed as catalysts or catalyst components for the preparation of chiral products in various types of reaction.

The present invention relates to a novel class of chiral phosphorus compounds of general formula I

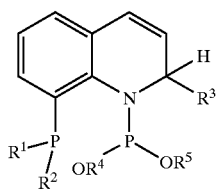

I wherein $R^1$, $R^2$, $R^3{}_1$, $R^4$, $R^5$ are chiral or achiral organic residues which are derived from substituted or unsubstituted straight or branched chain or cyclic aliphatic or aromatic groups and which, in the case of the pairs $R^1/R^2$ and $R^4/R^5$, may be interconnected. These compounds can be prepared simply and in few steps from derivatives of quinoline as inexpensive starting materials. The chiral information in the 2-position of the quinoline skeleton, which is critical to the selective formation of the desired optically active products, is produced during the synthesis and can be easily varied by selecting $R^3$. The two isomers with the different configurations in the 2-position can be effectively separated from each other. The compounds of formula I can be employed as efficient catalysts or catalyst components in the preparation of optically active products, wherein high activities and selectivities are achieved especially in enantioselective hydroformylation and hydrogenation.

Synthesis of the Phosphorus Compounds I

The synthesis of the phosphorus compounds I (Scheme 1) conveniently starts from 8-phosphinoquinolines II. Compounds II are already known for different residues $R^1$ and $R^2$ and can be easily prepared on a multigram scale via different routes (typical examples: Inorg. Chem. 1982, 21, 1007; J. Organomet. Chem. 1997, 535, 183). By means of these syntheses and suitable simple modifications, compounds of type II can be prepared in which $R^1$ or $R^2$ are the same or different chiral or achiral organic residues which are derived from substituted or unsubstituted straight or branched chain or cyclic aliphatic or aromatic groups and may be interconnected. Residues $R^1$ and $R^2$ can be independently selected from the groups methyl, ethyl, n-propyl, n-butyl, hexyl, $F(CF_2)_m(CH_2)_n$— (m=1–10, n=0–4), cyclo-hexyl, menthyl, allyl, benzyl, $CH_3O(CH_2)_2OCH_2$—, phenyl, tolyl, anisyl, trifluoro-methylphenyl, $F(CF_2)_m(CH_2)_nC_6H_4$—(m=1–10, n=0–4), bis(trifluoromethyl)phenyl, chlorophenyl, pentafluorophenyl, hydroxyphenyl, carboxyphenyl, $NaO_3SC_6H_4$—, naphthyl, fluorenyl, pyridyl or furyl, the groups mentioned not being intended to imply any limitation to the scope of application. When the two groups are interconnected, there may be formed substituted or unsubstituted chiral or achiral bridges which are derived, for example, from the skeletons —$(CH_2)_n$— (n=2–4), —CH($CH_3$)CH($CH_3$)—, —CH($CH_3$)CH$_2$CH($CH_3$)—, 1,1'-bipheny-2,2'-diyl or 1,1'-binaphth-2,2'-diyl, again no limitation being implied by this listing.

The reaction of II with nucleophilic reagents $R^3M$ yields compounds III, wherein $R^3$ refers to the same definition as $R^1$ or $R^2$. The addition in 2-position of the quinoline can be accomplished with Grignard compounds (M=MgHal, Hal=halogen) and many other organometallic compounds (e.g., M=Li, ZnR, SnR$_3$; R=alkyl or aryl residue), so that a wide variety of possible derivatives results. The addition in 2-position of the quinoline produces a chiral center, the stereochemistry at this center not being defined in the absence of an additional chiral auxiliary or catalyst.

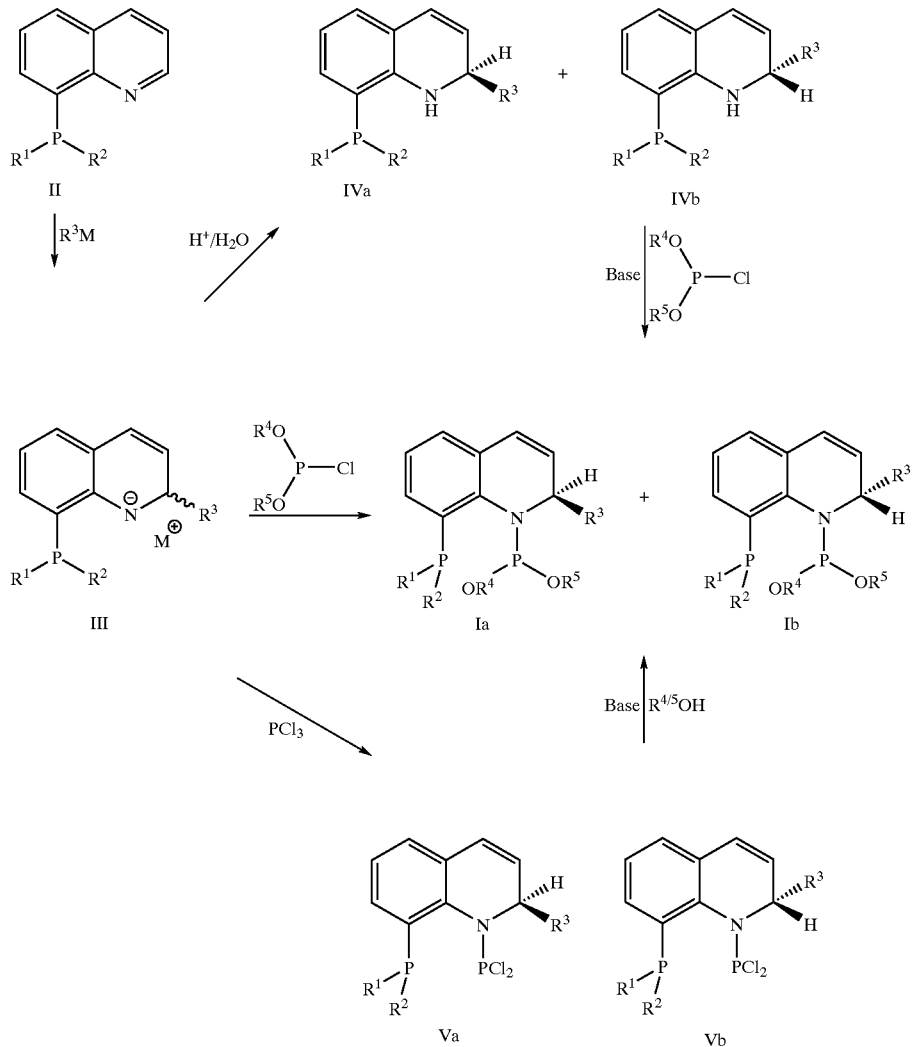

Compounds III can be converted to the 1,2-dihydroquinoline derivatives IV by hydrolysis. Reaction with chlorophosphinites $(R^4O)(R^5O)PCl$ in the presence of bases such as triethylamine or pyridine yields the desired phosphorus compounds of formula I. An alternative approach is the reaction of III with $PCl_3$ to form the dichlorophosphine derivatives V. Reaction with alcohols or diols in the presence of base again yields I. Compounds III can also be reacted directly with chloro-phosphinites $(R^4O)(R^5O)PCl$ without further addition of bases to I.

The residues $R^4$ and $R^5$ may be the same or different, achiral or chiral, and may be interconnected. Otherwise, the residues have the same definition as residues $R^1$ and $R^2$. Examples of alcohols and diols which may be used for the preparation of the corresponding compounds $(R^4O)(R^5O)$PCl or directly reacted with V include methanol, ethanol, iso-propanol, benzyl alcohol, cyclohexanol, allyl alcohol, phenol, methylphenol, chlorophenol, naphthol, furfurol, ethylene glycol, 1,3-propanediol, 1,3-pentanediol, cyclohexanediol, glycerol, monosaccharides, oligosaccharides, catechol, 2,2'-dihydroxy-1,1'-biphenyl, 3,3',5,5'-tetra-tert-butyl-2,2'-dihydroxy-1,1'-biphenyl,3,3'-di-tert-butyl-2,2'-dihydroxy-5,5'-dimethoxy-1,1'-biphenyl, 5,5'-dichloro-4,4',6,6'-tetramethyl-2,2'-dihydroxy-1,1'-biphenyl or 2,2'-dihydroxy-1,1'-binaphthyl, the listing not being intended to imply any limitation to the scope of application.

When optically active $(R^4O)(R^5O)P$ groups are used, compounds I are obtained as diastereomers which can be separated by crystallization, chromatography or other suitable separation methods. Alternatively, the separation of the two stereoisomers can be effected on the stage of the 1,2-dihydroquinoline derivatives IV, which can be resolved by conventional methods into enantiomers IVa and IVb (see, for example, Tetrahedron Asymmetry 1999, 10, 1079).

Table 1 gives a survey about representative examples of compounds of formula I which were produced and spectroscopically characterized by the mentioned methods. A detailed description for the preparation of the mixture of diastereomers $(R_a,R_C{}^*)$-quinaphos and the pure diastereomers $(R_a,R_C)$-quinaphos and $(R_a,S_C)$-quinaphos (quinaphos: $R^1=R^2=Ph$, $R^3=n$-Bu, $R^4$-$R^5=1,1'$-binaphth-2,2'-diyl) can be found in Example 1. The assignment of an absolute configuration to the chiral center in the 2-position of the quinoline skeleton is based on a comparison of NMR-spectroscopic data with related chiral derivatives of quinoline (Eur. J. Inorg. Chem. 1999, 8, 1203) and is prone to a corresponding uncertainty.

TABLE I
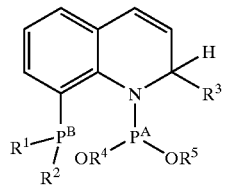
I
| Config. an C2 | R¹ | R² | R³ | R⁴ R⁵ | δ(P_A) ppm | δ(P_B) ppm | J_{P^A P^B} (Hz) |
|---|---|---|---|---|---|---|---|
| R_C<br>S_C | Ph | Ph | n-Bu | ![binaphthol] | 137.5<br>143.6 | −17.8<br>−16.4 | 191.7<br>131.2 |
| R_C<br>S_C | Ph | Ph | t-Bu | ![binaphthol] | 139.0<br>141.6 | −19.2<br>−19.1 | 180.2<br>85.2 |
| Racemate | Ph | Ph | n-Bu | ![di-t-Bu-di-OMe-biphenol] | 144.7 | −18.6 | 202.7 |
| R_C<br>S_C | R_f-C₆H₄-<br>R_f = (CH₂)₂(CF₂)₆F | R_f-C₆H₄-<br>R_f = (CH₂)₂(CF₂)₆F | n-Bu | ![binaphthol] | 136.9<br>143.3 | −18.3<br>−16.8 | 194.5<br>130.4 |

Application in Catalysis

The chiral phosphor compounds I can be used in an optically pure form, as a mixture of diastereomers or in the form of the pure diastereomers as effective catalysts or catalyst components in the synthesis of optically active products. Particularly preferred are syntheses in which compounds I are employed as components ("ligands") of transition metal catalysts. Such catalysts contain one or more transition metal centers which may be the same or different. Preferred metals include Cu, Ag, Au, Ni, Pd, Pt, Co, Rh, Ir, Fe, Ru, Os, Mn, Re, Cr, Mo, W, Ti or Zr. Particularly preferred are Cu, Ni, Pd, Pt, Rh, Ir or Ru.

The catalysts may be employed in the form of isolated compounds which already contain the metal and the ligand I, or may be formed in situ from I and suitable metal-containing components. As the metal-containing components, the metals themselves, simple salts or complex compounds of the corresponding metals can be used. The molar ratio between the ligand I and the metal center can be optimally adapted for the respective reaction and is usually between 1:1 and 10:1.

The catalytic syntheses using the ligands I can be performed in either absence or presence of a solvent, wherein the solvent can have a positive influence on activity or enantioselectivity, or can facilitate the separation of the product and catalyst. As the solvent, typical organic solvents, such as benzene, toluene, methylene chloride, ethanol, tetrahydrofuran or diethyl ether, may be used. Water is also suitable as a solvent when the ligand is sufficiently soluble in water due to suitable polar substituents (e.g., —COOH, $NH_3^+$, $SO_3^-$, see Angew. Chem. 1993, 105, 1588). The reactions may also be performed in supercritical carbon dioxide as the solvent if adequate solubility is ensured by suitable substituents (e.g., perfluoroalkyl residues, see PCT application WO 98/32533). To facilitate separation from the reaction products, the ligands I can be bound to solid supports using known methods (adsorption, inclusion, covalent bonding: Synthesis 1997, 1217). The scope of application of ligands I includes asymmetric reductions (e.g., hydrogenation, transfer hydrogenation), asymmetric carbon-carbon bond formation (e.g., hydroformylation, Heck coupling, allylic alkylation, hydrocyanation, hydrovinylation, polymerization) and asymmetric bond formation between carbon and heteroatoms (e.g., hydroboration, hydrosilylation, hydroamination, hydrophosphination), as illustrated in the following Examples using the quinaphos ligand.

Enantioselective Hydroformylation with Ligands I

Enantioselective hydroformylation is an efficient method for the synthesis of chiral, non-racemic aldehydes from olefins (Catalytic Asymmetric Synthesis, Ed.: I. Ojima, VCH, Weinheim, 1993, pages 273ff). This type of reaction has met with great interest especially as a possible approach to chiral building blocks for the production of flavoring agents, cosmetics, plant protectants, food additives (vitamins) and pharmaceuticals (Chirality 1991, 3, 355). In particular, there may be mentioned the preparation of the anti-inflammatory and analgetic drugs ibuprofen and naproxen by oxidation of the corresponding aldehydes, which can be obtained from vinyl arenes by means of enantioselective hydroformylation. In addition to enantioselectivity, in this reaction, chemoselectivity (side reaction is predominantly hydrogenation) and regioselectivity in favor of the branched chiral aldehyde are of particular importance. In the case of quinaphos, the best enantioselectivities are produced in the hydroformylation of styrene with the ($R_a$, $S_C$)-diastereomer (Examples 2–4). The hydrogenation as an undesirable side reaction is not detected in significant amounts. As compared with ligands of comparable activity and enantioselectivity, the highest regioselectivities are achieved in favor of the chiral aldehyde (Chem. Rev. 1995, 95, 2485–2506).

Preferred catalysts for the hydroformylation are formed on the basis of the metals Fe, Co, Ir, Ru, Pt, Rh, more preferably on the basis of Pt and Rh. The molar ratio of ligand/metal should be between 1:1 and 10:1, preferably between 1:1 and 4:1.

The molar ratio of substrate and catalyst can be widely varied, and preferably a ratio of between 100:1 and 10,000:1 is used. The gases $H_2$ and CO can be added to the reactor either separately or as a mixture. The partial pressure of the individual gases is within a range of from 1 to 100 bar. The total pressure of synthesis gas can be within a range of from 1 to 200 bar, preferably within a range of from 10 to 100 bar. The reaction temperature can be widely varied and is between −20° C. and 150° C., preferably between 20° C. and 80° C.

Enantioselective Hydrogenation with Ligands I

Enantioselective hydrogenation is an efficient method for the synthesis of chiral, non-racemic organic compounds (Catalytic Asymmetric Synthesis, Ed.: I. Ojima, VCH, Weinheim, 1993, pages 1ff), which is of great importance, in particular, to the preparation of biologically active substances. Enantioselective hydrogenation is known for a wide variety of functional groups, especially for substrates with prochiral C=C, C=N or C=O double bonds. The hydrogenation of dehydroamino acids is an attractive approach to natural and non-natural amino acids and has already found a technical application, for example, in the preparation of L-Dopa, a medicament against Parkinson's disease (Topics in Catalysis 1998, 5, 3).

Preferred catalysts for hydrogenation with ligands I are formed on the basis of the metals Pd, Pt, Co, Ir, Rh and Ru. The molar ratio of ligand/metal should be between 1:1 and 10:1, preferably between 1:1 and 2.5:1. In the case of quinaphos, the best enantioselectivities are achieved in the hydrogenation of itaconic acid dimethyl ester with the ($R_a$,$R_C$)-diastereomer (Examples 5, 7).

The molar ratio of substrate and catalyst can be widely varied and is preferably between 100:1 and 100,000:1. The catalyst system Rh(I)/quinaphos shows an activity and lifetime which are remarkably high for rhodium catalysts (Example 11). The hydrogenation rate of at least 36,000 catalytic cycles per hour is considerably higher than the activities typically observed for catalysts on the basis of rhodium catalysts with phosphorus compounds (about 200 cycles per hour, J. Chem. Soc. (A) 1967, 1574).

The partial pressure of hydrogen during hydrogenation should be within a range of from 0.3 to 200 bar, preferably between 10 and 100 bar. The reaction temperature can be widely varied and is between −20° C. and 150° C., preferably between 20° C. and 60° C.

Enantioselective Hydroboration with Ligands I

Enantioselective hydroboration is a typical example of a reaction with formation of a carbon-heteroatom bond. It has met with great interest since the boranes produced are interesting intermediates for further syntheses (e.g., formation of chiral alcohols, carbon-carbon bond formation, etc.) (Tetrahedron 1997, 53, 4957). In addition to the enantioselectivity of the carbon-boron bond formation, chemoselectivity (side reaction is predominantly reduction) and regioselectivity are also important characteristics of this reaction.

Preferred catalysts for the hydroboration with ligands I are formed on the basis of Rh. The molar ratio of ligand/ metal should be between 1:1 and 4:1, preferably between 1:1 and 2:1 (Examples 14, 17).

The molar ratio of substrate and catalyst can be widely varied and is preferably between 100:1 and 10,000:1. The reaction temperature can be widely varied and is between −80° C. and 100° C., preferably between 20° C. and 80° C.

EXAMPLES

Example 1

Synthesis of $(R_a,R_C^*)$-quinaphos, $(R_a,R_C)$-quinaphos and $(R_a,S_C)$-quinaphos In a Schlenk vessel, a solution of n-BuLi in pentane (1.6 M, 2 ml) was added with a syringe to 8-diphenylphosphinoquinoline (1.0 g, 3.2 mmol) in THF (40 ml) at −78° C. The solution was warmed to 0° C. and stirred at this temperature for 30 min. The dark-red solution obtained was transferred into a cooled dropping funnel and slowly added dropwise at −30° C. to a solution of (R)-1,1'-binaphthyl-2,2'-dioxy)chlorophosphine in THF (20 ml). The reaction mixture was warmed to room temperature over night with stirring. After removing the solvent under vacuum, the residue was extracted with toluene (50 ml). The extractant was removed under vacuum, and the residue was recrystallized from methylene chloride/ethanol at −20° C. to obtain 1.24 g (1.8 mmol, 56% of theory) of $(R_a,R_C^*)$-quinaphos as a 1:1 mixture of diastereomers in the form of a white microcrystalline powder.

To separate the diastereomers, 0.24 g of $(R_a,R_C^*)$-quinaphos was chromatographed on thoroughly heated silica gel (Merck type 9385, 230–400 mesh). With methylene chloride/pentane (1:5), $(R_a,R_C)$-quinaphos (0.12 g, 100% of theory) was eluted as the first fraction. Subsequently, $(R_a,S_C)$-quinaphos (0.05 g, 42% of theory) was eluted with pure methylene chloride.

Selected Analytical Data $(R_a,R_C)$-quinaphos $^1$H NMR ($C_6D_6$): δ=7.86 (d, J=8.7 Hz, 1H, Ar—H), 7.70–7.39 (m, 11H, Ar—H), 7.31 (m, 1H, Ar—H), 7.10–6.84 (m, 11H, Ar—H), 7.78 (m, 1H, Ar—H), 6.39 (d, $^3$J=9.5 Hz, 1H, CH=CH), 5.72 (dd, $^3$J=9.5 Hz, $^3$J=5.6 Hz, 1H, CH=CH), 4.01(m, 1H, CH), 1.40–0.90 (m, 6H, $CH_2$), 0.61 (t, $^3$J=7.2 Hz, 3H, $CH_3$).

$^{31}$P NMR ($C_6D_6$): see Table 1

$(R_a,S_C)$-quinaphos $^1$H-NMR ($C_6D_6$): δ=7.63–7.57 (m, 6H, Ar—H), 7.51–7.43 (m, 2H,Ar—H), 7.28–7.22 (m, 4H, Ar—H), 7.12–6.94 (m, 12H, Ar—H), 7.79 (m, 1H, Ar—H), 6.18 (d, $^3$J=9.6 Hz, 1H, CH=CH), 5.56 (dd, $^3$J=9.6 Hz, $^3$J=5.7 Hz, 1H, CH=CH), 3.88 (m, 1H, CH), 1.40–0.88 (m, 6H, $CH_2$), 0.73 (t, $^3$J=7.2 Hz, 3H, $CH_3$).

$^{31}$P NMR ($C_6D_6$): see Table 1

The mixture of diastereomers, $(R_a,R_C^*)$-quinaphos, shows the two sets of data from the individual diastereomers in a ratio of 1:1.

Examples 2–4

Enantioselective Hydroformylation of Styrene

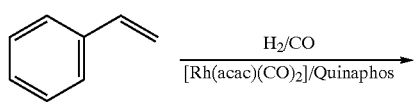

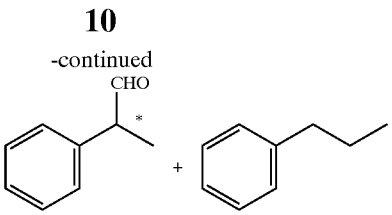

In a steel autoclave (V=11.4 ml) equipped with inspection glasses, a manometer, valves and thermocouples, one for the jacket temperature and one for the interior temperature, the complex [Rh(acac)(CO)$_2$] (0.52 mg, 2×10$^{-3}$ mmol, acac= acetylacetonate) and quinaphos (5.5 mg, 8×10$^{-3}$ mmol) were charged. Subsequently, styrene (0.5 ml) was added (molar ratio of substrate/rhodium =S/Rh). The autoclave was pressurized with synthesis gas (CO/H$_2$_1:1) at a pressure of 100 bar at room temperature, and heated to 40° C. After a reaction time t, the reactor was cooled down to room temperature, the pressure was released, and the reaction mixture was processed by conventional methods. The conversion, chemoselectivity, regioselectivity in favor of the branched aldehyde and enantiomeric excess (ee) were determined by gas chromatography (HP 5890 with FID, column: Ivadex 7, injector temp.: 240° C., column temp.: 60–200° C.; detector temp.: 300° C., carrier gas: H$_2$).

| Example | S/Rh | Quinaphos | L/Rh | t (h) | conv. (%) | chemo-sel. (%) | regio-sel. (%) | ee (%) |
|---|---|---|---|---|---|---|---|---|
| 2 | 2200 | $(R_aR_C^*)$ | 4 | 90 | 54.8 | >99 | 96.3 | 35.6 (S) |
| 3 | 2200 | $(R_aR_C)$ | 4 | 74 | 79.3 | >99 | 96.0 | 4.8 (S) |
| 4 | 2200 | $(R_aS_C)$ | 4 | 70 | 75 | >99 | 96.7 | 74.0 (S) |

Examples 5–10

Enantioselective Hydrogenation of Itaconic Acid Dimethyl Ester

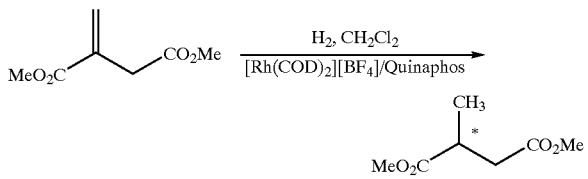

In a steel autoclave (V=11.4 ml) equipped with inspection glasses, a manometer, valves and thermocouples, one for the jacket temperature and one for the interior temperature, the complex [Rh(COD)$_2$][BF$_4$] (2×10$^{-3}$ mmol of Rh, COD=1,5-cyclooctadiene) and an amount of quinaphos sufficient to obtain the desired quinaphos-to-rhodium ratio (L/Rh) were dissolved in methylene chloride (2–6 ml). Subsequently, a corresponding amount of substrate (about 0.32–1.90 g) was added (molar ratio of substrate/rhodium=S/Rh, see Table). The autoclave was pressurized with hydrogen under a pressure of $P_{H_2}$ at room temperature (RT). After the solution has been vigorously stirred at the stated reaction temperature T for the reaction time t, the pressure was released, and processing was effected by conventional methods. The conversion and enantiomeric excess (ee) were determined by gas chromatography (HP 5890 with FID, column: γ-cyclodextrin, injector temp.: 180° C., column temp.: 60–87° C.; detector temp.: 250° C., carrier gas: H$_2$).

| Example | S/Rh | Quinaphos | L/Rh | T (° C.) | $p_{H2}$ (bar) | t (h) | conv. (%) | ee (%) |
|---|---|---|---|---|---|---|---|---|
| 5 | 1000 | $(R_aS_C)$ | 1.1 | RT | 30 | 24 | >99 | 64.2 (R) |
| 6 | 1000 | $(R_aS_C)$ | 2.2 | RT | 30 | 24 | >99 | 78.8 (R) |
| 7 | 1000 | $(R_aR_C)$ | 1.1 | RT | 30 | 24 | >99 | 95.6 (R) |
| 8 | 1000 | $(R_aR_C)$ | 2.2 | RT | 30 | 24 | >99 | 98.8 (R) |
| 9 | 1000 | $(R_aR_C)$ | 2.2 | 0 | 10 | 144 | 41.5 | 55.0 (R) |
| 10 | 1000 | $(R_aR_C)$ | 2.2 | RT | 0.8 | 24 | 5.5 | 24.6 (R) |

Example 11

Catalyst Activity and Lifetime

The experiment was performed in accordance with Examples 5–10, but using the isolated complex [{$(R_a,R_C)$-quinaphos)}Rh(COD)][$BF_4$] as the catalyst. The reaction was stopped already after 5 min by releasing the pressure, a sample was taken and analyzed (11a). Subsequently, substrate was again added to the reaction solution, and $H_2$ was added under pressure. After 10 min, the pressure was again released, and an analysis was performed (11b). In both cases, there was complete hydrogenation, so that a catalyst activity (TOF =catalytic cycles per hour) of 36,000 $h^{-1}$ can be estimated as a lower limit of activity.

| Example | S/Rh | T (° C.) | $p_{H2}$ (bar) | t (min) | conv. (%) | TOF ($h^{-1}$) | ee (%) |
|---|---|---|---|---|---|---|---|
| 11a | 1000 | 27 | 50 | 5 | >99 | >12,000 | 98.2 (R) |
| 11b | 6000 | 27 | 70 | 10 | >99 | >36,000 | 99.4 (R) |

Examples 12–13

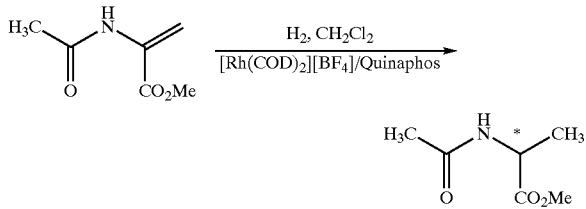

Examples 12–13 were performed by analogy with Examples 5–10.

Example 14

Enantioselective Hydroboration of Styrene

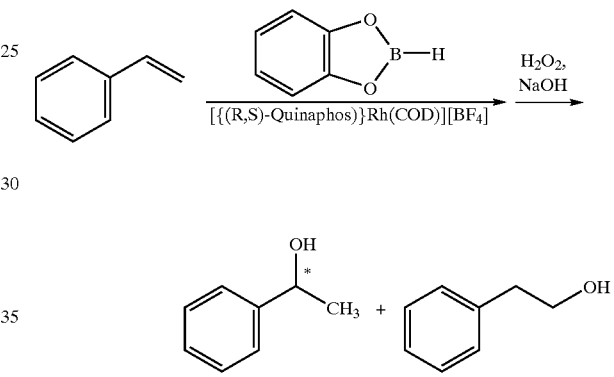

Into a Schlenk vessel, [{$(R_aR_C)$-quinaphos)}Rh(COD)][$BF_4$] (4×10$^{-3}$ mmol) and an amount of quinaphos sufficient to obtain the desired quinaphos-to-rhodium ratio (L/Rh) were charged. The catalyst was dissolved in 3 ml of solvent (solv), and styrene (0.045 ml) was added (molar ratio of substrate/rhodium =S/Rh, see Table). After the addition of catecholborane (0.048 ml), the solution was stirred at the stated reaction temperature T for the reaction time t, followed by oxidative processing by conventional methods. The conversion, chemoselectivity, regioselectivity and enantiomeric excess (ee) of the secondary alcohol were determined by gas chromatography (HP 5890 with FID, column: Ivadex 7, injector temp.: 220° C., column temp.: 60–160° C.; detector temp.: 250° C., carrier gas: $H_2$).

| Example | Quinaphos | S/Rh | L/Rh | T (° C.) | $p_{H2}$ (bar) | t (h) | conv. (%) | ee (%) |
|---|---|---|---|---|---|---|---|---|
| 12 | $(R_aR_C)$ | 1000 | 2.2[a] | RT | 30 | 85 | 8.0 | 12.4 (S) |
| 13 | $(R_aR_C)$ | 1000 | 1.0[b] | RT | 30 | 25 | >99 | 97.8 (S) |

[a] is situ catalyst from quinaphos and [Rh(COD)$_2$][BF$_4$];
[b] isolated complex [$_aR_C$)-quinaphos)Rh(COD)][BF$_4$] as catalyst.

| Example | S/Rh | L/Rh | solv | T (°C.) | t (h) | conv. (%) | chemosel. (%) | regiosel. (%) | ee (%) |
|---|---|---|---|---|---|---|---|---|---|
| 14 | 100 | 1 | toluene | 25 | 3 | >99 | >99 | 91.8 | 30.4 (S) |
| 15 | 100 | 1 | toluene | −20 | 14 | 48.5 | 93.7 | 76.3 | 19.0 (S) |
| 16 | 100 | 1 | toluene | −78 | 20 | 4.7 | 56.4 | 88.9 | 15.3 (S) |
| 17 | 100 | 2 | toluene | 25 | 3 | 3.8 | 93.5 | 78.4 | 20.8 (S) |
| 18 | 100 | 2 | THF | 25 | 3 | 2.4 | 92.5 | 69.1 | 5.0 (S) |

What is claimed is:

1. Chiral phosphorus compounds of formula I:

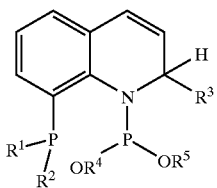

wherein $R^1$, $R^2$, $R^3$, $R^4$, $R^5$ are chiral or achiral substituted or unsubstituted straight-chain, branched-chain or cyclic aliphatic or aromatic groups and which, in the case of the pairs $R^1/R^2$ and $R^4/R^5$, may be interconnected to form a ring together with the atoms to which they are bonded.

2. The chiral phosphorus compounds according to claim 1, wherein $R^1$, $R^2$, $R^3$, $R^4$ or $R^5$ can be independently selected from the groups methyl, ethyl, n-propyl, n-butyl, hexyl, $F(CF_2)_m(CH_2)_n$ (m=1–10, n=0–4), cyclohexyl, menthyl, allyl, benzyl, —$CH_2O(CH_2)_2OCH_3$, phenyl, tolyl, anisyl, trifluoromethylphenyl, $F(CF_2)_m(CH_2)_nC_6H_4$— (m=1–10, n=0–4), bis(trifluoromethyl)phenyl, chlorophenyl, pentafluorophenyl, hydroxyphenyl, carboxyphenyl, $NaO_3SC_6H_4$—, naphthyl, fluorenyl, pyridyl and furyl.

3. The chiral phosphorus compounds according to claim 1, wherein $R^1$ and $R^2$ together form $(CH_2)_n$— (n=2–4), —$CH(CH_3)CH(CH_3)$—, —$CH(CH_3)CH_2CH(CH_3)$—, 1,1'-bipheny-2,2'-diyl or 1,1'-binaphth-2,2'-diyl, each of which is unsubstituted or substituted, and chiral or achiral.

4. The chiral phosphorus compounds according to claim 1, wherein $R^4$ and $R^5$ are introduced using the alcohols methanol, ethanol, isopropanol, benzyl alcohol, cyclohexanol, allyl alcohol, phenol, methylphenol, chlorophenol, naphthol, furfural, ethylene glycol, 1,3-propanediol, 1,3-pentanediol, cyclohexanediol, glycerol, monosaccharides, oligosaccharides, catechol, 2,2'-dihydroxy-1,1'-biphenyl, 3,3',5,5'-tetra-tert-butyl-2,2'-dihydroxy-1,1'-biphenyl, 3,3'-di-tert-butyl-2,2'-dihydroxy-5,5'-dimethoxy-1,1'-biphenyl, 5,5'-dichloro-4,4',6,6'-tetramethyl-2,2'-dihydroxy-1,1'-biphenyl or 2,2'-dihydroxy-1,1'-binaphthyl.

5. A catalyst comprising a phosphorus compound according to claim 1.

6. A process for preparing one or more optically active products, said process comprising preparing said optically active products in the presence of a catalyst according to claim 5.

7. The process according to claim 6, wherein said catalyst consists of said phosphorus compound and a transition metal or a transition metal compound.

8. The process according to claim 6, wherein said preparing comprises enantioselective hydroformylation.

9. The process according to claim 6, wherein said preparing comprises enantioselective hydrogenation.

10. The process according to claim 6, wherein said preparing comprises enantioselective hydroboration.

* * * * *

UNITED STATES PATENT AND TRADEMARK OFFICE
CERTIFICATE OF CORRECTION

PATENT NO. : 6,720,281 B2
DATED : April 13, 2004
INVENTOR(S) : Leitner et al.

It is certified that error appears in the above-identified patent and that said Letters Patent is hereby corrected as shown below:

Column 1,
Lines 27-28, "despite of the wide variety of" should read -- despite the wide variety of --.

Column 2,
Line 1, "$R^3_1$" should read -- $R^3$ --.

Column 10,
Line 17, "$CO/H_{2=}1:1$" should read -- $CO/H_2=1:1$ --.

Column 11,
Line 42, "Examples 12-13" should read -- Examples 12-13 Hydrogenation of N-acetamidoacyrlic acid methyl ester --.

Column 13,
Line 32, "$(CH_2)_n(m=1-10, n=0-4)$" should read -- $(CH_2)_n$ - (m=1-10, n=0-4) --.

Signed and Sealed this

Twenty-first Day of March, 2006

JON W. DUDAS
*Director of the United States Patent and Trademark Office*